United States Patent [19]
Barry et al.

[11] 4,318,482
[45] Mar. 9, 1982

[54] METHOD FOR MEASURING THE VELOCITY OF A PERTURBED JETTING FLUID IN AN ELECTROSTATIC PARTICLE SORTING SYSTEM

[75] Inventors: Donald E. Barry, Norwood; Igino Lombardo, Sharon, both of Mass.

[73] Assignee: Ortho Diagnostics, Inc., Raritan, N.J.

[21] Appl. No.: 68,235

[22] Filed: Aug. 20, 1979

[51] Int. Cl.³ .......................................... B07C 5/342
[52] U.S. Cl. ............................ 209/3.1; 209/579; 209/906; 250/222 PC; 346/75; 356/72; 361/226; 364/413
[58] Field of Search ................................. 209/3.1–3.3, 209/571, 579, 906, 127 R; 356/39, 72, 73, 335, 338; 250/222 R, 222 PC; 361/226; 364/413 346/75

[56] References Cited

U.S. PATENT DOCUMENTS

| | | | |
|---|---|---|---|
| 3,380,584 | 4/1968 | Fulwyler | 209/3 |
| 3,600,955 | 8/1971 | Bischoff | 346/75 X |
| 3,710,933 | 1/1973 | Fulwyler et al. | 209/3 |
| 3,761,941 | 9/1973 | Robertson | 346/1 |
| 3,769,627 | 10/1973 | Stone | 346/75 |
| 3,826,364 | 7/1974 | Bonner et al. | 209/3 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 346/75 |
| 3,920,702 | 10/1975 | Corll | 356/72 |
| 3,941,479 | 3/1976 | Whitehead | 356/102 |
| 3,953,860 | 4/1976 | Fukimoto et al. | 346/75 |
| 3,963,606 | 6/1976 | Hogg | 209/3 |
| 3,982,251 | 9/1976 | Hochberg | 346/1 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/1 |
| 4,063,252 | 12/1977 | Jensen et al. | 346/75 |
| 4,148,718 | 4/1979 | Fulwyler | 209/3.1 |

OTHER PUBLICATIONS

Buehner et al.; "Two-Level Ink Jet Deflection Control System"; IBM Tech. Discl.; vol. 16, No. 10, 3–74.
"Laser Flow Microphotometry for Rapid Analysis and Sorting of Mammalian Cells", Mullaney, et al., Annals New York Academy of Sciences, vol. 267, pp. 176–190.
"Feedback for Synchronized Pressure Jet Using Optical Sensor", IBM Technical Disclosure Bulletin, vol. 16, No. 12, May 1974, pp. 3877–3878.
"Phase Detection on Ink Jet Droplets", IBM Technical Disclosure Bulletin, vol. 16, No. 3, Aug. 1973, p. 880.

*Primary Examiner*—Joseph J. Rolla
*Attorney, Agent, or Firm*—Audley A. Ciamporcero, Jr.

[57] ABSTRACT

A method for the measurement of fluid velocity and fluid flow rate is described which may be applied to a system in which fluid is caused to exit through an orifice to form a free jet. Optical as well as fluidic properties of the jetting fluids are used to determine the mean velocity of the jet between its point of exit from the orifice and at least a preselected detection point. From the mean velocity determination, the fluid flow rate may also be determined. A marker signal perturbation is applied to the jetting fluid at the orifice, and is detected downstream at a stream sensing point which is located a preselected distance from that orifice.

15 Claims, 5 Drawing Figures

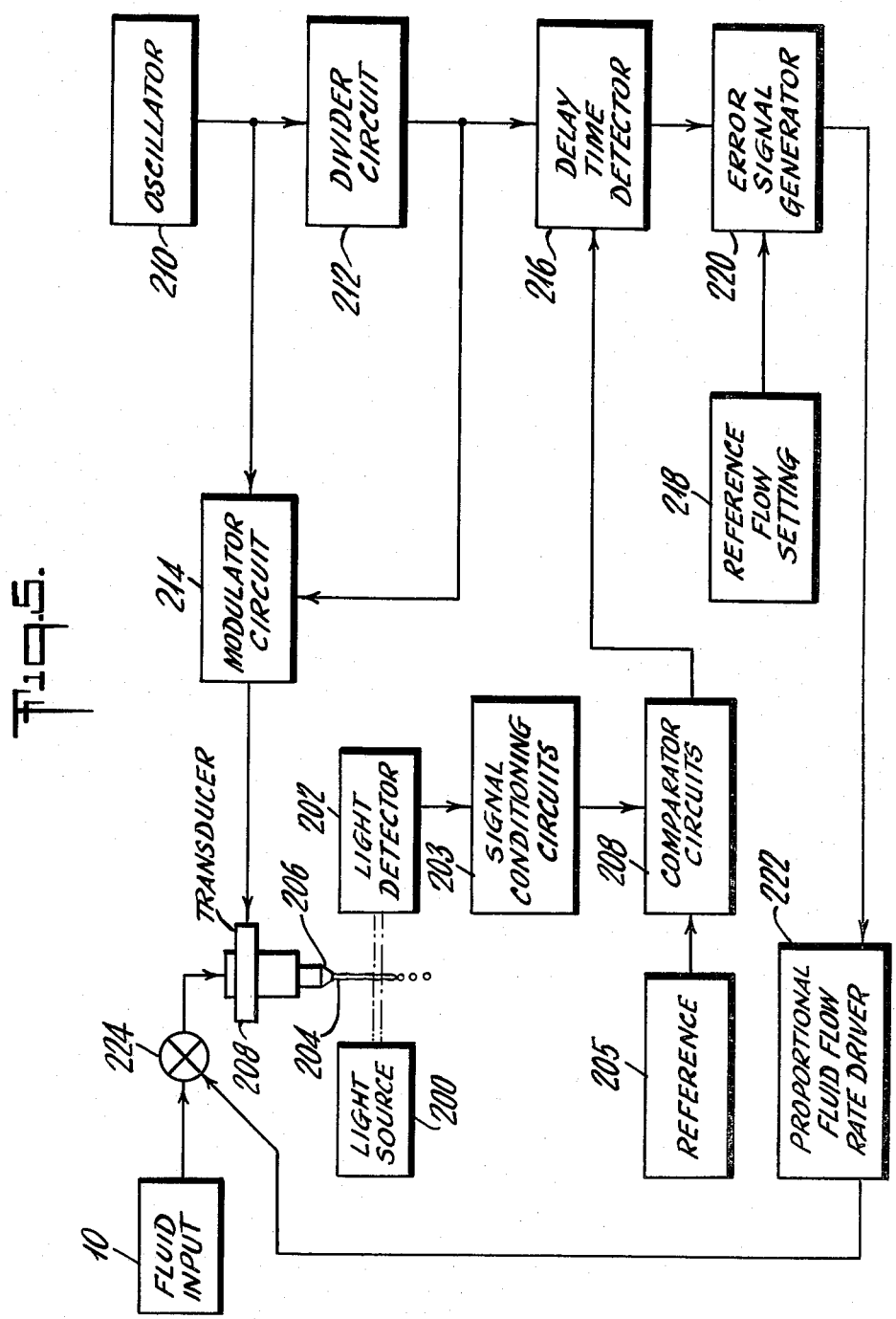

METHOD FOR MEASURING THE VELOCITY OF A PERTURBED JETTING FLUID IN AN ELECTROSTATIC PARTICLE SORTING SYSTEM

CROSS REFERENCE TO RELATED APPLICATIONS

The present application is related to the following applications, each of which is assigned to the assignee of the present application and are hereby incorporated by reference as if fully set forth herein: The invention of Igino Lombardo, Donald E. Barry, and W. Peter Hansen entitled, "Method For Detecting And Controlling Flow Rates Of The Droplet Forming Stream Of An Electrostatic Particle Sorting Apparatus", Ser. No. 068,231, filed Aug. 20, 1979; the invention of Igino Lombardo and W. Peter Hansen entitled, "Method And Apparatus For Positioning The Point Of Droplet Formation In The Jetting Fluid Of An Elecrostatic Sorting Device", Ser. No. 068,113, filed Aug. 20, 1979; the invention of Igino Lombardo and Donald E. Barry entitled, "Automatic Relative Droplet Charging Time Delay System For An Electrostatic Particle Sorting System Using A Relatively Moveable Stream Surface Sensing System", Ser. No. 068,259, filed Aug. 20, 1979; the invention of Igino Lombardo and Donald E. Barry entitled, "Method For Automatically Setting The Correct Phase Of The Charge Pulses In An Electrostatic Flow Sorter", Ser. No. 068,234, filed Aug. 20, 1979; and the invention of Richard A. Dussault and Igino Lombardo entitled, "A Servo System To Control The Spatial Position Of Droplet Formation Of A Fluid Jet In A Cell Storing Apparatus", Ser. No. 068,112, filed Aug. 20, 1979.

As to Ser. No. 068,231, please see generally pages 15-25; as to Ser. No. 068,113 see generally pages 15-24; as to Ser. No. 068,259, see generally pages 15-22; as to Ser. No. 068,234, see generally pages 15-21; and as to Ser. No. 068,112, see generally pages 15-27.

BACKGROUND OF THE INVENTION

The present invention relates generally to the field of electrostatic flow sorters, and more particularly to those sorters which are adapted to sense the presence and/or character of particles in a laminar flow stream and to selectively sort those particles by breaking that stream into a number of discrete droplets, and sorting those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, an electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interest arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Microphotometry For Rapid Analysis And Sorting Of Mammalian Cells", Mullaney, et al., Annals New York Academy Of Sciences, Vol. 267, pages 176-190 (see in particular, pages 180 and FIGS. 3 and 4).

Such particle sorters are also disclosed in U.S. Pat. Nos. 3,710,933 (Fulwyler, et al.) and 3,380,584 (Fulwyler) and 4,148,718 (Fulwyler). In these patents, sorting is accomplished in accordance with a selected parameter which may be size, volume, presence or radioactivity, color, fluorescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14-49.

As described particularly in U.S. Pat. No. 3,710,933, (Fulwyler, et al.), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al. to be in the order of 1400 microseconds) can be estimated so that an appropriate droplet charging generator will operate in combination with a pulse height analyzer and cell separation logic to charge the selected cell containing droplets for subsequent electrostatic sorting.

A number of factors affect the ability of a given apparatus to selectively sort one or more types of target cells from a continuous cell stream. Even assuming that the detection equipment for identifying each cell to be sorted is 100% accurate, differences in flow rate, temperature, fluid viscosity, and transducer performance can affect the time delay or location of the desired target-cell-containing droplets at the breakpoint, which is the point at which a charge pulse must be administered to insure that the target cell will be subsequently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al.), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are adjusted to provide the necessary time delay to allow for travel time of the particle from the point of particle scatter detection to the point where the stream breaks into drops. Bonner states:

"With the present arrangement the delay time between observation of a particle and its capture by a separating droplet is predictable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22–32.

As further explained in the Bonner, et al. disclosure, the duration as well as the time of application of the charging pulse is critical to the separation of at least the droplet containing the target particle to be sorted. After describing a preferred charging pulse which will charge at least three drops, Bonner, et al. states:

"Obviously, if instrument tolerances, variations, drift and like permitted, then a drop charging time sufficient to charge only two successive drops, or a single drop, could be employed." U.S. Pat. No. 3,826,364, Col. 8, lines 2–6.

As also pointed out by Bonner, et al., a drop breaking from a given flow stream carries with it a charge which is proportional to the potential between the droplet stream and the surrounding electrodes or charging surfaces at the time the drop separates from the stream. If the drop breaks off from the jet stream during the transition time from the drop charge pulse, either during the leading or trailing edge of that pulse, some intermediate value between zero and the desired full charge may be imparted to the target droplet. In the Bonner, et al. apparatus, on/off transitions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the defleted drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet forming aperture to the point of break off. Hogg proposes the use of a movable scale in place of the ground glass of prior art projection microscopes, this scale being linked to a potentiometer of an RC oscillator to thereby control the oscillator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23–36. Accordingly, Hogg represents a more automated version of the stroboscopic projection microscopic techniques discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establish uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al.) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wherein a light source and photocell located downstream from the breakpoint of a perturbed stream is used to sense the passage of discrete droplets and to time delayed charges subsequently applied thereto. Stone states:

"Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore, that the charging process must be carefully synchronized with the timing of the drop break off. This involves the use of complex phasing control sensors and loops. This in turn, increases the cost of the equipment. . . . It is an object of this invention to provide an ink drop charging system which does not depend upon the synchronization of the charging with the break off time.

It is another object of this invention to produce an ink drop charging system, which charges drops after they break off from the ink jet stream." U.S. Pat. No. 3,769,627 (Stone), Col. 1, lines 18-35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

"The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53-68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phases of fundamental and harmonic frequencies. Taub states:

"The light passing through the slit 44 is influenced by the wave passing a given point on the perimeter of the jet, and accordingly is a representation of the frequency components of the jet at this particular point, as well as being indicative of the shape of a given droplet when it breaks-off downstream. It is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100 A centered in the laser wavelength, is used so measurements may be made in room light. The light passed by the filter 48 is then transmitted to a photomultiplier tube 50 which measures the intensity of the light. Therefore, the output voltage of the photomultiplier tube 50 is proportional to the diameter of the jet blocking the slit, which is to say, to the local diameter of the jet at the point being probed . . . . It is to be appreciated that the signal output . . . may be applied to analyzing means 80 by other timing means such as a stepping motor, or alternatively may be applied concurrently to inputs of devices 82, 84 and 86, rather than in the time sequence described." U.S. Pat. No. 4,047,183. See Col. 6, lines 27-68, Col. 7, lines 1-26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877-8, entitled "Feedback For Synchronized Pressure Jet Using Optical Sensor", and IBM Technical Disclosure Bulletin, Vol. 16, No. 3, August 1973, Page 880, entitled "Phase Detection On Ink Jet Droplets".

For other disclosures relating to various ink jet printing synchronization systems, please refer to U.S. Pat. No. 4,025,926 (Fujimoto, et al.) entitled, "Phase Synchronization For Ink Jet System Printer"; U.S. Pat. No. 4,045,770 (Arnold, et al.) entitled, "Method and Apparatus For Adjusting The Velocity Of Ink Drops In An Ink Jet Printer"; U.S. Pat. No. 3,953,860 (Fujimoto, et al.) entitled, "Charge Amplitude Detection For Ink Jet System Printer"; U.S. Pat. No. 3,761,941 (Robertson) entitled, "Phase Control For A Drop Generating and Charging System"; U.S. Pat. No. 3,836,912 (Ghougasian, et al.) entitled, "Drop Charge Sensing Apparatus For Ink Jet Printing System"; U.S. Pat. No. 3,982,251 (Hochberg) entitled, "Method and Apparatus For Recording Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles In A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention provides a system particularly adapted for use with electrostatic flow sorters wherein perturbed jetting fluids are caused to exit from an orifice and proceed at least through a droplet formation or droplet breakpoint whereupon the continuous stream becomes a series of discrete droplets. In such systems, it is desirable to know the particular velocity travelled by the flow stream between the orifice from which the jetting fluid emanates and a point downstream of that orifice which is located at or just above the breakpoint. The present invention provides a novel method and apparatus for marking a perturbed flow stream with an easily detectable marking signal which is then detected downstream at a stream sensing point. The time delay between creation of the marker signal at the orifice and its arrival at the stream sensing point is used to determine the velocity of the stream. In a preferred embodiment of the present invention, the stream velocity which is thus determined is compared to a stream velocity reference setting. If the actual velocity of the perturbed stream is found to vary from the desired velocity reference setting, an error signal is produced for proportionally varying the flow rate of the stream until the desired reference setting velocity is reestablished.

In the preferred embodiment, a marker signal is produced at periodic intervals by modulating the amplitude of the transducer, and thus of the orifice and stream perturbation. A stream surface sensing means for sensing the light scatter and extinction of the stream at a stream sensing point disposed above said breakpoint and at a preselected distance from said perturbation means, is provided which produces a surface character output signal which is proportional to the stream surface character. When the marker signal, in the form of a varied, i.e., increased, amplitude perturbation in the stream reaches the stream surface sensing means, a corresponding amplitude variation occurs in the surface character output signal. This amplitude variation is compared to a reference by comparitor circuits which detect the arrival of the marker signal at the stream sensing point, and transmit that information to a delay time detector which records the elapsed time between the creation of that marker signal and its arrival at the stream sensing point. In this manner, an extremely simple yet reliable method is provided for measuring the velocity of a perturbed stream in an electrostatic particle sorting system.

Accordingly, a primary object of the present invention is the provision of an improved electrostatic particle sorting system comprising automated means for determining the perturbation stream velocity at least between an exit orifice and a stream sensing point located a preselected distance therefrom. This and other objects of the present invention will become apparent from the following more detailed description.

BRIEF DESCRIPTION OF THE DRAWINGS

FIG. 5 is a diagrammatic block drawing of a preferred embodiment electrostatic particle sorting system for automatically maintaining the velocity of the jetting fluid between the orifice and a preselected stream sensing point located downstream of that orifice.

DETAILED DESCRIPTION OF THE DRAWINGS

Figure 1:
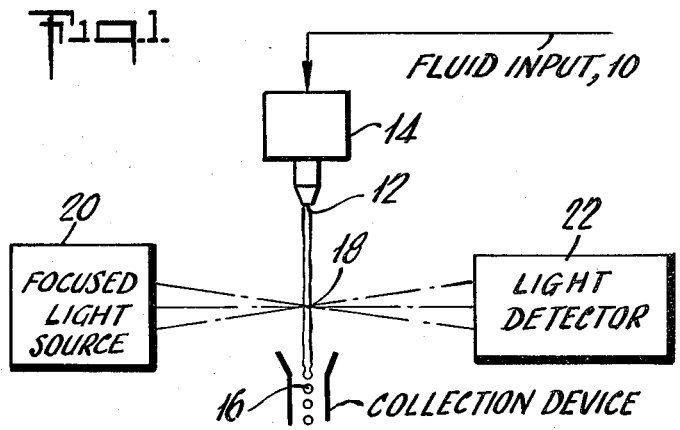
FIG. 1 is a diagrammatic illustration of a portion of an electrostatic particle sorting system wherein a reservoir supplied flow stream is caused to exist through a transducer-coupled orifice and is subjected to a stream surface sensing means for sensing the light scatter and extinction character of the stream prior to its formation into discrete droplets at the droplet breakpoint, and subsequent collection.

Although specific forms of the invention have been selected for illustration in the drawings, and the following description is drawn in specific terms for the purpose of describing these forms of the invention, this description is not intended to limit the scope of the invention which is defined in the appended claims.

Referring to the drawings, and more particularly to FIGS. 1 and 5, the present invention relates to a particle sorting system comprising a flow means for establishing the flow of a continuous particle containing stream. In the figures, this flow means is represented as a fluid input 10. In FIG. 1, which is a simple embodiment sufficient to measure flow rate and velocity, the fluid input 10 is seen to pass through an orifice 12 which is coupled with a transducer 14. Together, transducer 14 and orifice 12 comprise a perturbation means for perturbing said stream with at least a preselected frequency and amplitude to cause said stream to form a breakpoint 16 at which said stream becomes a series of discrete droplets. A stream surface sensing means for sensing the light scatter and extinction of said stream at a stream sensing point 18 disposed above said breakpoint 16 and at a preselected distance ($\Delta D$) from said perturbation means is provided, which stream sensing means produces a surface character output signal which is proportional to the surface character of said stream. In the preferred embodiment, the stream surface sensing means comprises a focused light source 20 which is focused on the stream at the stream sensing point 18 and which is axially aligned with a light detector 22 for detecting the extinction and scattering of the focused light caused by the perturbed flow stream at the stream sensing point 18.

Figure 2:
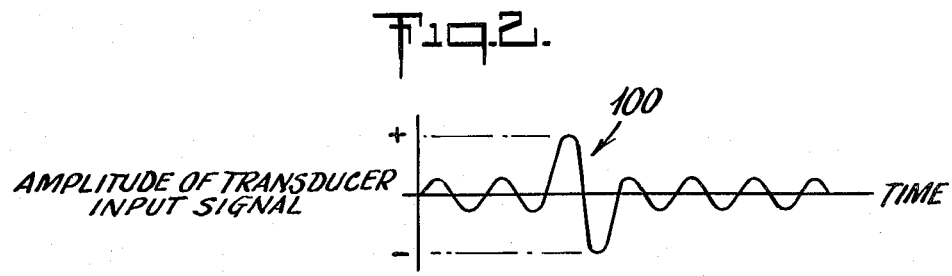
FIG. 2 is a waveform graph of amplitude verses time for a preferred embodiment transducer input signal including a marker amplitude waveform.
Figure 3:
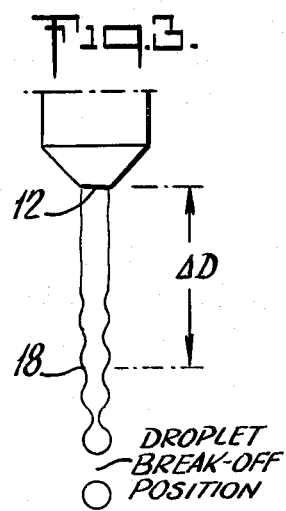
FIG. 3 is a diagrammatic illustration of a portion of the jetting flow stream illustrated in FIG. 1 wherein the relationship between the orifice and detection point is illustrated.
Figure 4:
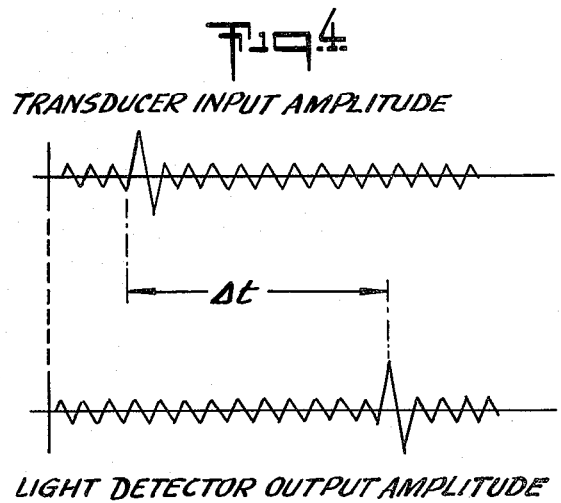
FIG. 4 is a comparative amplitude verses time graph of the transducer input waveform compared to the light detector output waveform, the delay between the creation of the marker signal and its detection being illustrated by $\Delta t$ in this figure.

Referring now to FIG. 2, it will be seen that by properly driving the transducer 14 to create a marker signal, it is possible to accurately determine the velocity of the flow stream between the orifice 12 and the sheath sensing point 18. In FIG. 2, the normal waveform of the transducer input signal is illustrated with the exception that the third full cycle of that signal is seen to have a substantially increased amplitude. This cycle of increased amplitude will serve as a marker signal 100 for marking the flow stream at the orifice, as described more fully hereinafter. Referring now to FIG. 3, the distance between the orifice 12 and the detection point 18 is seen to comprise a distance marked ΔD in FIG. 3. The periodic modulation of the transducer amplitude, as represented in FIG. 2, produces a marker signal which is transmitted via mechanical coupling from the transducer to the orifice, causing the stream to be likewise modulated. The modulation of the stream at the orifice is minimal and hard to detect, but as the stream moves down, the effects grow exponentially until the stream finally decomposes into droplets of variable size. The propagation delay between input signal change and the appearance of that change at the orifice is a small constant due to the transducer transfer slew and the slight flexibility of the coupling from transducer to orifice. The propagation delay between the orifice amplitude change and the detection of that change on the stream at the light-detector position 18 corresponds to the velocity of the stream travelling a fixed distance from orifice to detection point. In FIG. 4, total propagation delay is illustrated by comparing the transducer input amplitude with the light detector output amplitude, Δt representing the time delay between modulation of the input and the detection of that modulation downstream.

Velocity of the stream accordingly may be calculated from the following empirically determined formula:

$$\text{velocity} = \Delta D/(\Delta t - k)$$

where ΔD equals the distance from orifice to detection point,
Δt equals the time delay between modulation of the input and the detection of that modulation downstream,
and k equals the propagation delay of the transducer-orifice assembly. The volume flow rate per unit time may be determine for a known diameter orifice by the formulation:

$$F/t = \frac{d^2}{4} \pi \frac{\Delta D}{\Delta t - k}$$

where F equals the volume of flow, t a unit of time, and d the diameter of the orifice.

Referring now to FIG. 5, a preferred embodiment system is disclosed which automatically controls the fluid velocity of jetting fluid transmitted between an orifice and stream sensing point, as described above. In this system, the stream surface sensing means again comprises a light source 200 which is focused on the stream 204 at a stream sensing point, and a light detector 202 for measuring the degree of extinction and scatter of the light caused by the perturbed stream 204. As with the system described in FIG. 1, fluid from the fluid input 10 is directed through an orifice 206 which is coupled with a transducer 208. An oscillator 210 is provided for driving the transducer 208 and orifice 206 to perturb this stream at a preselected frequency and amplitude. A divider circuit 212 and modulator circuit 214 together comprise the marker signal means for selectively varying the perturbation caused by the perturbation means to create a marker signal in said stream. The divider circuit 212 monitors the oscillator output for the purpose of producing a periodic trigger signal which not only triggers the modulator circuit 214 but also delay time detector 216. In accordance with the preferred embodiment of the present invention, the periodicity of the trigger signal should be selected to be relatively infrequent with respect to the frequency of the oscillator, to thereby assure that the overall function of the flow sorter is not substantially impared. Upon receipt of the trigger signal from the divider circuit, the modulator circuit should preferably modulate the amplitude of the oscillator signal transmitted to the transducer 208. In this manner, spikes in the transducer input amplitude similar to the spikes illustrated in FIGS. 2 and 4 will be created and will lead to the creation of a marker signal in said stream. As discussed above, it is anticipated that the delay time detector 216 will start its timing cycle slightly before the actual creation of the marker signal in the stream, due to the propagation delay of the transducer-orifice assembly. This propagation delay may, however, be compensated for in the delay time detector, or in the reference flow setting, as described more fully hereinafter.

The output from the light detector, which may be a photodiode or photomultiplier, is subjected to conventional signal conditioning circuits such as amplification, band pass filtering, and/or other conditioning which is known to improve the signal to noise ratio of such signals. In order to sense the arrival of the marker signal at the stream sensing point, a marker signal detection means is provided which comprises a reference amplitude setting 206 and comparator circuits 208 which compare the surface character output signal with the reference setting to determine whether a marker signal has in fact been sensed at the stream sensing point. In the event that a marker perturbation is in fact sensed by the comparator circuits 208, a stop signal B is transmitted to the delay time detector, which produces an output signal C which represents the elapsed time between modulation of the transducer and downstream detection of the marker signal. An error signal generator 220 is provided which receives and compares the above-mentioned time delay output C with a reference flow setting time delay value D, and which generates a proportional error signal in response to detected differences therebetween. This error signal drives proportional fluid flow rate driver 222 through control valve 224 to increase or decrease the fluid flow rate of fluid delivered to orifice 206. In this manner, the velocity of the fluid flow stream 204 is automatically adjusted until the output of the time delay detector 216 corresponds to the reference flow setting 218.

In accordance with the above description, it will be appreciated that an extremely simple yet efficient system has been described for sensing and automatically establishing and controlling the fluid velocity of a perturbed laminar flow stream.

It will be understood that various changes in the details, materials and arrangement of parts which have been herein described and illustrated in order to explain the nature of this invention may be made by those skilled in the art within the principle and scope of the invention as expressed in the following claims. As used herein, "perturbed" or "perturbation" is meant to include not only mechanical/vibratory methods for creating discontinuities in the stream, but also discontinuities which are induced by other means such as alteration of stream surface tension, for example, by electrical, thermal, or optical means. Likewise, periodic or aperiodic perturbations are meant to be included.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. An electrostatic particle sorting system comprising:
   (a) flow means for establishing the flow of a continuous particle containing stream;
   (b) perturbation means for perturbing said stream with at least a preselected frequency and amplitude to cause said stream to form a breakpoint at which said stream becomes a series of discrete droplets;
   (c) stream surface sensing means for sensing at least the light scatter characteristic of said stream at a stream sensing point disposed above said breakpoint and at a preselected distance from said perturbation means; and for producing a surface character output signal which is proportional thereto;
   (d) marker signal means for selectively varying the perturbation caused by said perturbation means to create a marker signal in said stream; and
   (e) marker signal detection means for monitoring said surface character output signal to detect the arrival of said marker signal at said stream sensing point.

2. The invention of claim 1 wherein said stream surface sensing means for sensing at least the light scatter character of said stream further comprises a light extinction means for sensing the light extinction character of said stream at said stream sensing point.

3. The invention of claim 1 wherein said system further comprises time delay detection means for determining the time delay between the creation of said marker signal and its said arrival at said stream sensing point.

4. The invention of claim 3 wherein said system further comprises a reference flow setting and an error signal generator means for producing an error signal proportional to differences between said reference flow setting and said time delay.

5. The invention of claim 4 wherein said flow means further comprises a proportional fluid flow rate driver responsive to said error signal for altering the flow rate of said continuous particle containing stream.

6. The invention of claim 1 wherein said perturbation means comprises a transducer and an oscillator for driving said transducer at a preselected amplitude and frequency.

7. The invention of claim 6 wherein said marker signal means comprises means for periodically modulating said amplitude.

8. The invention of claim 6 wherein said marker signal means comprises means for periodically modulating said frequency.

9. An electrostatic particle sorting method comprising the steps of:
   (a) establishing the flow of a continuous particle containing stream;
   (b) perturbing said stream with at least a preselected frequency and amplitude at a perturbation point defined therealong to cause said stream to form a breakpoint at which said stream becomes a series of discrete droplets;
   (c) sensing at least the light scatter character of said stream at a stream sensing point disposed above said breakpoint and at a preselected distance from said perturbation point, and generating a surface character output signal which is proportional to said light scatter character of said stream at said point;
   (d) selectively varying the perturbation caused at said perturbation point to create a marker signal in said stream; and
   (e) monitoring said surface character output signal to detect the arrival of said marker signal at said stream sensing point.

10. The invention of claim 9 wherein said step of perturbing said stream with a preselected frequency and amplitude further comprises the step of selectively modulating said amplitude of perturbation to produce said marker signal.

11. The invention of claim 9 wherein said step of perturbing said stream further comprises the step of selectively modulating said frequency perturbation of said steam to produce said marker signal.

12. The method of claim 9 wherein said step of sensing at least the light scatter character of said stream further comprises the step of sensing at least the light extinction character of said stream.

13. The invention of claim 9 wherein said method further comprises the step of detecting the time delay between the creation of said marker signal at said perturbation point and its arrival at said stream sensing point.

14. The invention of claim 13 wherein said method further comprises the step of generating a reference flow setting and comparing that reference flow setting with said time delay to generate an error signal proportional to the differences between said reference flow setting and said time delay.

15. The invention of claim 14 wherein said method further comprises the step of altering the fluid flow rate of said continuous particle containing stream in response to said error signal.

* * * * *